US008152856B2

(12) United States Patent
Hall et al.

(10) Patent No.: US 8,152,856 B2
(45) Date of Patent: Apr. 10, 2012

(54) LAYER ARRANGED ON IMPLANT FOR BONE OR TISSUE STRUCTURE, SUCH AN IMPLANT, AND A METHOD FOR APPLICATION OF THE LAYER

(75) Inventors: Jan Hall, Goteborg (SE); Jukka Lausmaa, Goteborg (SE)

(73) Assignee: Nobel Biocare AB (publ.), Göteborg (SE)

( * ) Notice: Subject to any disclaimer, the term of this patent is extended or adjusted under 35 U.S.C. 154(b) by 0 days.

(21) Appl. No.: 12/748,867

(22) Filed: Mar. 29, 2010

(65) Prior Publication Data

US 2010/0185293 A1     Jul. 22, 2010

Related U.S. Application Data

(63) Continuation of application No. 09/980,006, filed as application No. PCT/SE00/01026 on May 23, 2000, now Pat. No. 7,713,307.

(30) Foreign Application Priority Data

May 31, 1999   (SE) ..................................... 9901974

(51) Int. Cl.
    *A61F 2/28*        (2006.01)
(52) U.S. Cl. ..................................... 623/23.5
(58) Field of Classification Search ............. 623/23.5, 623/23.53, 23.55, 23.74, 23.76; 606/76
    See application file for complete search history.

(56) References Cited

U.S. PATENT DOCUMENTS

| | | | |
|---|---|---|---|
| 3,605,123 A | 9/1971 | Hahn | |
| 3,855,638 A | 12/1974 | Pilliar | |
| 4,330,891 A | 5/1982 | Branemark et al. | |
| 4,599,085 A | 7/1986 | Riess et al. | |
| 4,635,379 A | 1/1987 | Kroneld | |
| 4,687,551 A | 8/1987 | Furneaux et al. | |
| 4,801,300 A | 1/1989 | Kurze et al. | |
| 4,955,909 A | 9/1990 | Ersek et al. | |
| 5,034,186 A | 7/1991 | Shimamune et al. | |
| 5,084,050 A | 1/1992 | Draenert | |
| 5,098,434 A | 3/1992 | Serbousek | |
| 5,607,474 A | 3/1997 | Athanasiou et al. | |
| 5,642,996 A | 7/1997 | Mochida et al. | |

(Continued)

FOREIGN PATENT DOCUMENTS

DE          210 607 C       6/1984

(Continued)

OTHER PUBLICATIONS

Nobel Biocare Annual Report 2003. p. 18.

*Primary Examiner* — Eduardo C Robert
*Assistant Examiner* — David Comstock
(74) *Attorney, Agent, or Firm* — Connolly Bove Lodge & Hutz LLP (57) ABSTRACT

A layer is arranged on an implant for bone or tissue structure. The layer constitutes a boundary or barrier between the actual or unoxidized body of the implant and the structure for the purpose of increasing retention and has, in this context, a substantial thickness. The layer is designed with a channel network which gives the layer a substantial porosity. The channel network is designed with mouths which face towards the structure and whose respective cross-sectional diameters, at the surface of the layer facing towards the structure, are substantially less than the respective extents of the channels in and down into the layer as seen from the said surface.

18 Claims, 4 Drawing Sheets

U.S. PATENT DOCUMENTS

| | | |
|---|---|---|
| 5,665,118 A | 9/1997 | LaSalle et al. |
| 5,876,446 A | 3/1999 | Agrawal et al. |
| 6,008,432 A | 12/1999 | Taylor |

FOREIGN PATENT DOCUMENTS

| | | | |
|---|---|---|---|
| JP | 55-120864 A | | 9/1980 |
| JP | 05-003319 A | | 1/1993 |
| JP | 05-345014 A | | 12/1993 |
| JP | 07506732 T | | 7/1995 |
| JP | 07-275276 A | | 10/1995 |
| JP | 09-173436 A | | 7/1997 |
| JP | 11-043799 A | | 2/1999 |
| WO | WO-9313815 A1 | | 7/1993 |
| WO | WO-98/51231 | * | 11/1998 |

* cited by examiner

| Electrolyte | U (V) | I (mA) | Time (s) | Pore diam. (μm) | Pore density ($10^8/cm^2$) | Porosity (%) | Oxide thickness (μm) |
|---|---|---|---|---|---|---|---|
| 0.35M $H_2SO_4$ | 250 | 300 | 400 | n.a. | | | 9.2-13.5 |
| 0.35M $H_2SO_4$ | 250 | 800 | 300 | n.a. | | | 19.1-21.3 |
| 1.0M $H_2SO_4$ | 200 | 200 | 400 | n.a. | | | 5.8-6.5 |
| 0.35M $H_2SO_4$ +160 min | 200 | 200 | 300 | 0.28-0.92 | 0.45 | 5.65 | 3.5-7.0 |
| 0.35M $H_2SO_4$ etched | 200 | 200 | 300 | 0.06-0.43 | 2.48 | 6.47 | 2.2-2.8 |
| 0.15M $H_2SO_4$+ | 300 | 200 | 300 | 0.31-2.27 | 0.078 | 4.16 | 2.9-6.5 |
| 0.25M $H_2SO_4$+ | 300 | 200 | 300 | 0.31-2.65 | 0.080 | 7.84 | 3.6-6.5 |
| 0.35M $H_2SO_4$+ | 300 | 1400 | 300 | 0.31-4.06 | 0.060 | 10.69 | 3.6-11.0 | ized TI-6Al-4V orthopedic materials" in "Journal of
LAYER ARRANGED ON IMPLANT FOR BONE OR TISSUE STRUCTURE, SUCH AN IMPLANT, AND A METHOD FOR APPLICATION OF THE LAYER

CROSS REFERENCE TO RELATED APPLICATIONS

This application is a Continuation Application of U.S. application Ser. No. 09/980,006, filed May 9, 2002, which is a 35 U.S.C. §371 National Stage Application of International Application Serial No. PCT/SE2000/001026, filed May 23, 2000, which claims priority to Swedish Patent Application No. 9901974-7, filed May 31, 1999, the entire contents of each are incorporated herein by reference in their entirety.

TECHNICAL FIELD

The present invention relates to a layer which can be arranged on an implant for bone or tissue structure and which is intended to constitute a boundary or barrier between the body of the implant and the structure for the purpose of increasing retention and which has, in this context, a substantial thickness. The invention also relates to an implant with such a layer, and to a method for producing the said layer on the implant.

PRIOR ART

In connection with implants, it is already well known to arrange porous surfaces and oxide layers on titanium-based material for various aims and purposes. Depending on the purpose, it has been proposed to use oxide layer thicknesses within a very wide range which extends from a few angstroms upwards. Reference may be made in purely general terms to various publications, for example the article published by Dunn et al. "Gentamicin sulfate attachment and release from anodized TI-6Al-4V orthopedic materials" in "Journal of Biomedical Materials Research, Vol. 27, 895-900 (1993) and to the article "Formation and characterization of anodic titanium oxide films containing Ca and P" by Hitoshi Ishizawa and Makoto Ogino in "Journal of Biomedical Materials Research, Vol. 29, 65-72 (1995)". Reference may also be made in purely general terms to the patent literature, for example to U.S. Pat. Nos. 4,330,891 and 5,354,390 and to European Patent Application 95102381.1 (676179).

Considerable resources are being expended on research and development aimed at producing implants which can improve the process of incorporation of the implant in bone and tissue structures, for example in the jaw bone.

DESCRIPTION OF THE INVENTION

The present invention is based on the recognition that the oxide layer structure used in this context can have a decisive influence for improving implantation and incorporation processes. In the prior art there is no collective grasp of the actual build-up of the oxide layer structure and the need, at least in some circumstances, to be able to use very thick oxide layers. The aim of the invention is primarily to solve this problem.

In connection with application of implants in bone and tissue structures, it is important to establish good corrosion resistance and, for example in connection with the use of hydrogen fluoride (HF), to avoid the occurrence of brittleness. It is also important for the oxide layer to be able to have a structure which eliminates or to a large extent counteracts mechanical stress concentrations in implants inserted in the bone or equivalent, cf. the built-in stresses which can occur in connection with etched surfaces. Further demands and requirements are that the process of incorporation of the implant in the bone or tissue can be improved. The invention solves this problem too.

In connection with the implant, it is possible in some cases (i.e. in one embodiment) to use bone-growth-initiating and bone-growth-stimulating agents and substances, for example those belonging to the superfamily TGF-β. It is important to be able to apply the agent or the substance to or on the implant in a technically simple, and economically advantageous manner. The invention also solves this problem and proposes, through the novel oxide layer structure, a suitable depot function which can be used in long-term and optimal bone growth situations and incorporation functions for the implant in the bone or equivalent.

When producing thick oxide layers (for example, thicknesses of 5-20 μm), it is important to be able to offer technically reliable and also economically advantageous methods. The present invention also proposes methods satisfying the conditions for production of oxide layers of the type in question. The method is based on the recognition that the electrolyte composition and/or the electrical voltages used can be of decisive importance.

SOLUTION

The feature which can principally be regarded as characterizing a layer according to the invention is that it is designed with a channel network which gives the layer a substantial porosity, and that the channel network is designed with mouths which face towards the structure and whose respective cross-sectional areas, at the surface of the layer facing towards the structure, are substantially less than the respective extents of the channels in and down into the layer as seen from the said surface.

In a preferred embodiment, the channel network comprises contiguous channel branches which extend through at least the greater part of the layer as seen from the said surface and in to the transition to the body of the implant. The layer can be established on an undulating or uneven surface present on the implant from the start and having a high roughness value (for example 0.4-5 μm) for the purpose of increasing the layer volume. The channel network can also have channel branches which extend in directions which are different from the depth direction of the layer (or the radial direction of the implant). The layer has a thickness which gives substantial corrosion resistance in relation to the previously proposed oxide layer arrangements. In one embodiment, the channel network can also be arranged with a mouth arrangement towards the bone or tissue structure, permitting increased release of bone growth substance from the channel network via the said mouths. The layer can be given an average thickness in accordance with the attached patent claims. Preferred values in respect of the surface area sizes of the mouths of the channel network, the total channel or pore volume in the layer, the surface roughness and the porosity are likewise indicated in the attached patent claims.

An implant according to the invention can principally be regarded as being characterized by the fact that each layer present on the implant is designed with a channel network which gives the layer a substantial porosity, and by the fact that the channel network is designed with mouths which face towards the structure and whose respective cross-sectional areas, at the surface of the layer facing towards the structure, are substantially less than the respective extents of the channels in and down into the layer as seen from the said surface.

In one embodiment, the implant can consist of a screw implant for application in bone, for example dentine. In a further embodiment, the oxide layer can form a depot for applied bone-growth-initiating or bone-growth-stimulating agent or substance. The agent or the substance can migrate from the depot to the bone or tissue structure by means of concentration diffusion, which can be optimized by means of the channel network's mouth arrangement facing towards the bone or tissue structure. In a preferred embodiment, the layer consists of or comprises a titanium oxide layer.

A method according to the invention starts out from anodic oxidation of the implant material in question. The method can principally be characterized by the fact that diluted inorganic acids, diluted organic acids and/or small quantities of hydrofluoric acid or hydrogen peroxide are added to the electrolytic composition which is used in the method, and by the fact that the energy source is chosen to operate with a voltage value of at least 150 volts. Thus, for example, voltage values in the range of 200-400 volts can be used.

In a preferred embodiment, the voltage varies at times for the same implant in order to create different channel or pore sizes within the same surface area or surface areas of the implant. In a further embodiment, different porosities or pore or channel characteristics can be obtained by means of the position of the implant in the electrolyte being changed, together with the choice of the electrolyte composition and/or the voltage used. The oxide thickness can also be varied by means of the said parameters.

Another aspect of the invention relates to layer for arranging on an implant for bone or tissue structure and which constitutes a boundary or barrier between the body of the implant and the structure for the purpose of increasing retention and which has, in this context, a thickness, wherein the layer is designed with a channel network which gives the layer a porosity, and wherein the channel network is designed with mouths which face towards the structure and whose respective cross-sectional diameters, at a surface of the layer which faces towards the structure, are less than the respective extends of the channels in and down into the layer as seen from the said surface and wherein the layer consists of or comprises a titanium oxide layer.

A further aspect of the invention relates to implant for bone or tissue structure and comprising one or more layers which constitute at least one boundary between the body of the implant and the structure for the purpose of increasing retention and which each have, in this context, a thickness, wherein each layer is designed with a channel network which gives the layer a porosity, and in that the channel network is designed with mouths which face towards the structure and whose respective cross-sectional diameters, at a surface of the layer which faces towards the structure, are less than the respective extents of the channels in and down into the layer as seen from the said surface.

Still another aspect of the invention relates to method for producing, by anodic oxidation, on an implant comprising or consisting of titanium, thick oxide layers on one or more titanium surfaces which are intended to be placed against or arranged next to one or more tissue and/or bone growth areas, where at least part or parts supporting the one or more titanium surfaces are prepared and immersed in electrolyte and the implant is brought into contact with an electrical energy source above the electrolyte surface and the oxidation process is established by also connecting to the energy source a counter-electrode arranged in the electrolyte, wherein diluted inorganic acids, diluted organic acids and/or small quantities of hydrofluoric acids or hydrogen peroxide are added to a composition of the electrolytic, and wherein the energy source is chosen to operate with voltage values of at least 150 volts.

ADVANTAGES

By means of what has been proposed above, an improved implantation process is obtained, and, using the proposed oxide layer thicknesses at the upper end of the proposed range, the invention goes against the ideas which have hitherto been accepted in the technical field, thus opening up new avenues within the art. The concentration diffusion in conjunction with the use of bone-growth-initiating and bone-growth-stimulating substances can be considerably facilitated by the proposed channel make-up of the structure. The implant can be made commercially available with a finished oxide layer having the stated properties, and the novel method meets the conditions for economically advantageous layer production and implant production.

DESCRIPTION OF THE FIGURES

A presently proposed embodiment of a layer, an implant and a method according to the invention will be described below with reference to the attached drawings, in which.

DETAILED EMBODIMENT

Figure 1:
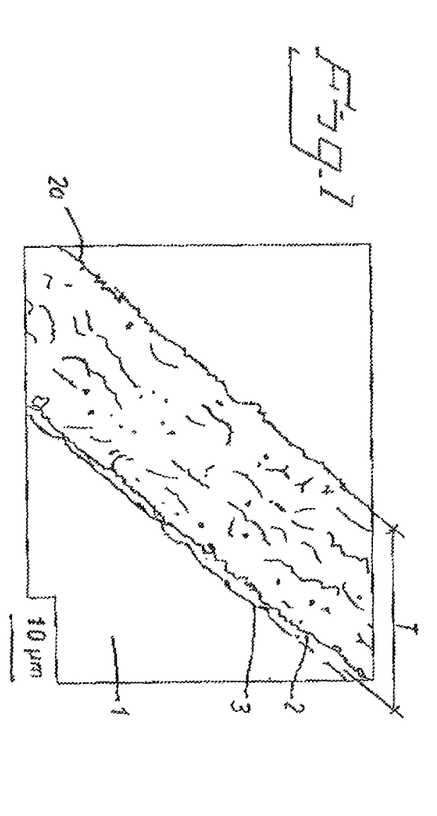
FIG. 1 shows, in longitudinal section, an illustrative embodiment of a titanium oxide layer produced on an implant body, the oxide layer starting from a relatively plane surface on the implant body.

In FIG. 1, reference number 1 indicates parts of an implant body. As will be described below, the implant body has been treated in an oxidation function, resulting in an oxidation layer 2 having been formed on its outer surface. The oxidation layer can be built up on a surface structure which is relatively smooth from the outset, as has been indicated by 3 in FIG. 1. The oxide layer 2 has a considerable thickness T. The layer can assume values of between 0.5 and 10 µm, with the values preferably being towards the upper limit of the range. According to the invention, the invention will function primarily in the range of 2-10 µm, although values as low as 0.5 µm may be used in certain exceptional cases. The outer surface 2a of the oxide layer must have a surface roughness within the range of 0.4-5 µm. According to what is described below, the oxide layer 2 has a high degree of porosity and encloses a channel network of specific type.

Figure 2:
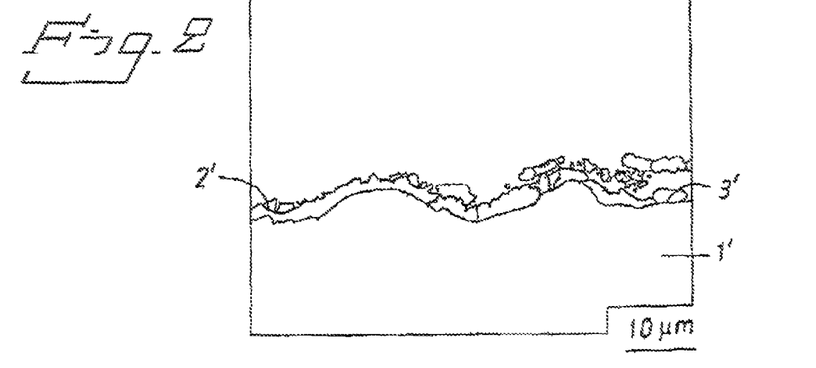
FIG. 2 shows, in longitudinal section, an example of the position of the oxide layer on an undulating surface or on a surface with a high degree of surface roughness.

FIG. 2 shows an example which differs from that in FIG. 1 and where the oxide layer 2' has been built up on a surface structure 3' located on the implant 1' and having a relatively high degree of surface roughness, which has been obtained in a manner known per se upon production of the implant (e.g. by etching). The embodiment according to FIG. 2 satisfies conditions for a relatively greater oxide layer volume than in the case according to FIG. 1.

Figure 3:
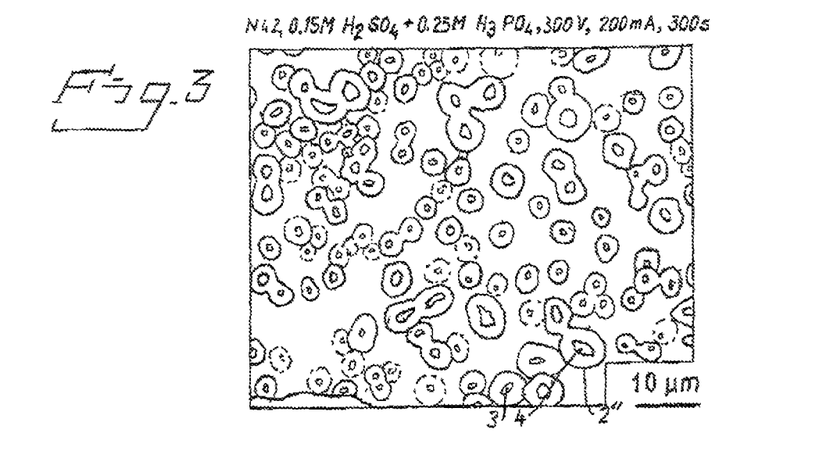
FIG. 3 shows a plan view, from, outside, of an example of a mouth arrangement for a channel network arranged in the oxide layer.

FIG. 3 shows, from the outside of the oxide layer 2", mouths 33, 4 leading from the channel network mentioned above.

In FIGS. 1, 2 and 3, the scale is shown at the bottom right-hand corner, i.e. the size 10 μm length in each figure.

Figure 4:
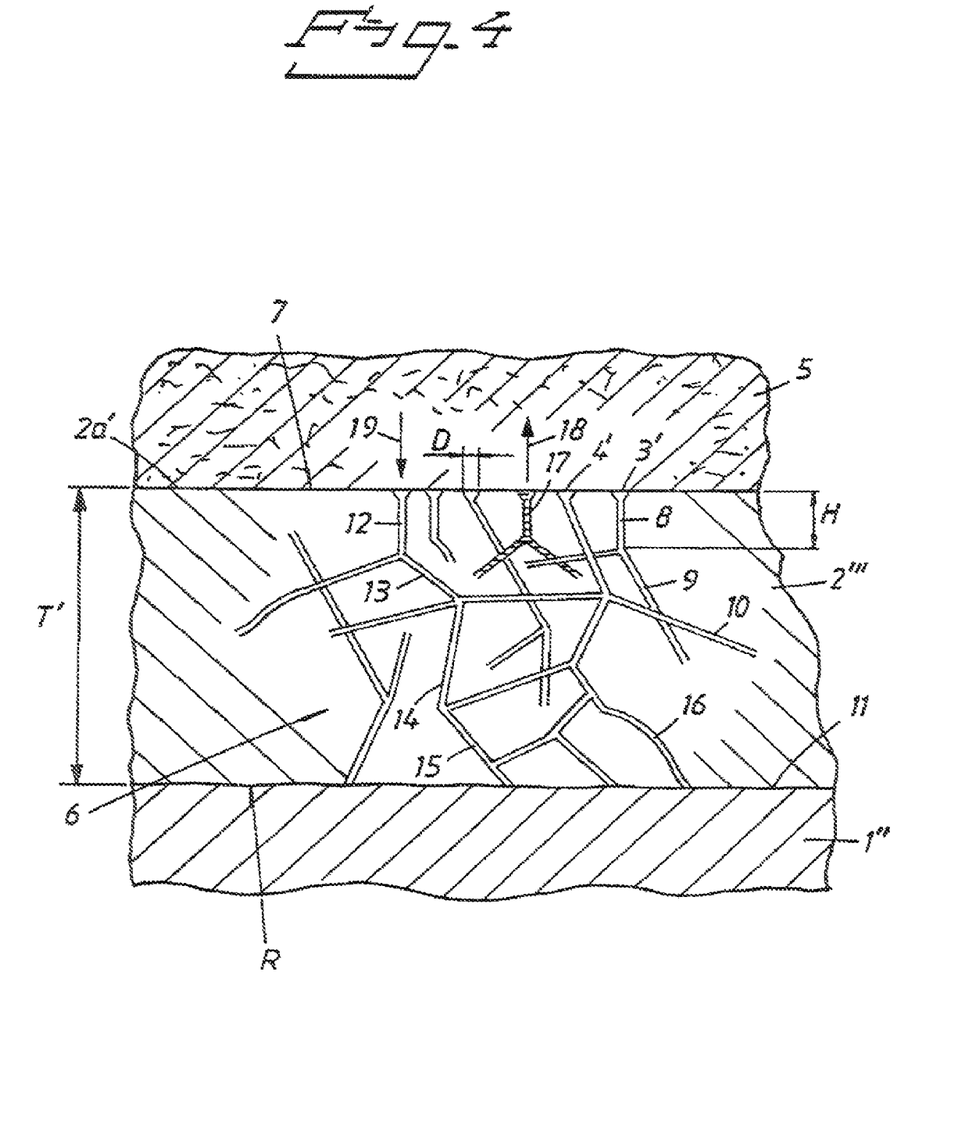
FIG. 4 shows, in vertical section and in diagrammatic form, a channel network for an oxide layer produced on an implant body, where the implant with associated oxide layer is applied in a partially shown bone and/or tissue structure in the human body, and in the oxide layer there is a channel network with a mouth arrangement facing towards the structure.

In FIG. 4, the implant is indicated by 1" and the oxide layer produced on the implant is indicated by 2'". In FIG. 4, a bone or tissue structure is indicated symbolically by 5. The structure can consist, for example, of a jaw bone in which the implant can be screwed down into the bone or equivalent. The implant can thus consist of or comprise titanium material, which means that the layer 2'", consists of a titanium oxide layer. The screw or the thread of the implant is not indicated in FIG. 4, but reference may be made to the already disclosed prior art and to known implants. The corresponding thread in the jaw bone 5 is not shown either, but here again reference may be made to the prior art. The oxide layer 2'" which is designed with the considerable thickness T', e.g. a thickness in the range of 5-25 μm, is provided with a channel network which is indicated symbolically by the arrow 6. In accordance with the above, the channel network has mouths or openings 33', 4'. The channel network branches down and/or in to the oxide layer, as seen from the outside 7 of the oxide layer. The channel network comprises different channel parts, for example 8, 9, 10. Channel routes can be established through the channel network which are made up of different channel parts and run from the outside 2a' of the layer 2'" and down or in towards a transition 11 between the implant and the oxide layer. Such a continuous channel formation is established with the channel parts or channel branches 12, 13, 14, 15 in the figure. A characteristic of the channel or pore formation according to the invention is that the surface areas or the diameter D of each mouth is substantially less than the respective channel boundary or pore depth, for example a pore depth H. According to the above, the pore depth or channel depth can be significant and correspond, for example, to the said thickness T'. The channels can extend in the direction of depth of the oxide layer 2'" and/or in directions which are different than this direction, or in the radial direction R of the implant. The channel branches or the channel parts can be straight and/or curved, a curved channel branch having been indicated by 16 in FIG. 4.

It will be appreciated that such a channel system can constitute a depot for substance which stimulates and/or initiates bone growth, and this has been symbolized by 17 in FIG. 4. A substance thus introduced into the channel network can, by means of concentration diffusion, migrate out into the bone or tissue structure, as has been symbolized by the arrow 18 in FIG. 4. Correspondingly, bone or tissue organisms can pass into the system in conjunction with the said diffusion as symbolized by arrow 19 in FIG. 4. It will be appreciated that the mouths can be given different sizes and can create conditions for bone growth with a specific penetration function in the mouth arrangement, contributing to the degree of incorporation of the implant in the structure. The oxide layer of high porosity can be formed with $1 \times 10^7$-$1 \times 10^{10}$ pores (channel mouths)/$cm^2$. The diameter sizes can be chosen in the range of 0.1-10 μm, and one and the same surface area of the oxide layer can have pores or channel mouths of different diameters or surface areas. A total volume for the channel network according to FIG. 4 can be chosen in a range of $5 \times 10^{-2}$ and $10^{-5}$ $cm^3$.

Figure 5:
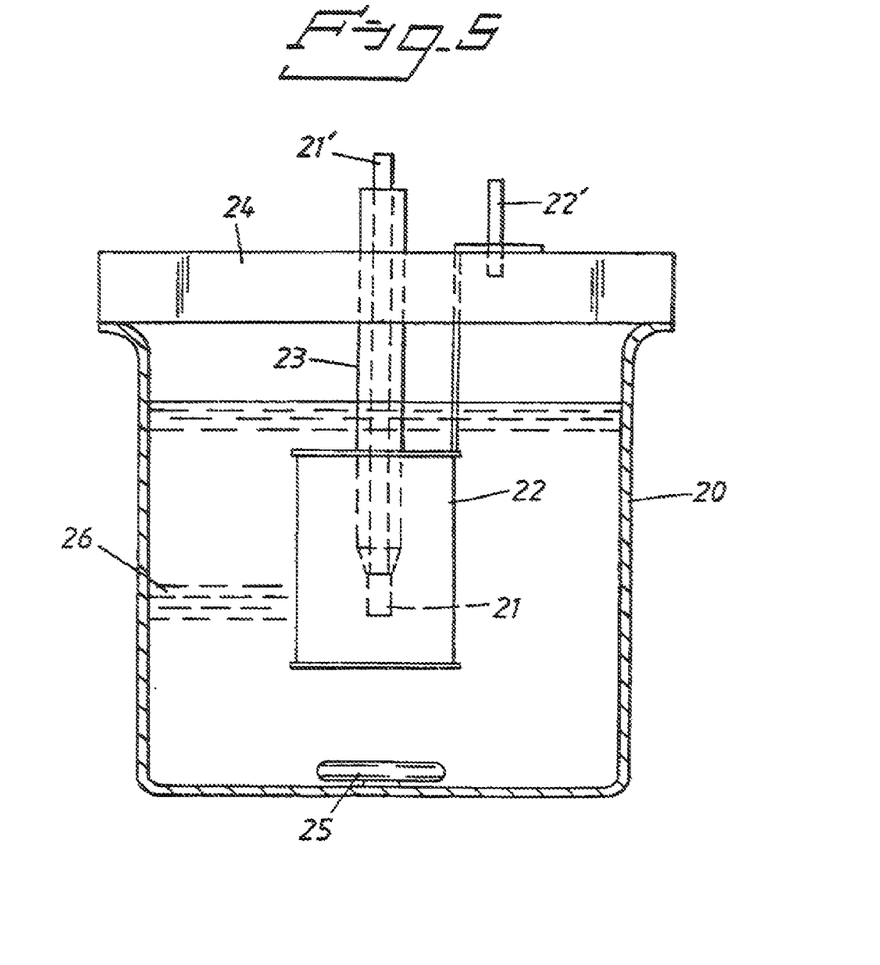
FIG. 5 shows a side view of equipment for anodic oxidation of an implant.

The titanium oxide layers according to the above are preferably produced by so-called anodic oxidation, which is an electrochemical process. The principle and the procedure for producing the layers in question are described with reference to FIGS. 5 and 6. In FIG. 5, a container is indicated by 20. A titanium anode is indicated by 21, and a porous meshed cathode is indicated by 22. A Teflon insulation of the titanium anode is indicated by 23, and the anodes extend through a Teflon cover 24. A magnetic agitator is also included. The attachments for anode and cathode are indicated by 21' and 22', respectively. The implant or the parts of the implant which are to be prepared are preferably mechanically worked by turning, milling, polishing, etc. The implant or parts in question comprise titanium surfaces which are to be treated in the electrochemical process. The implant or parts in question are mounted on a holder which is immersed in a bath in the container consisting of an electrolyte 26. Those parts of the implant which are not to be treated are masked by a liquid-tight protective sleeve or alternatively with a suitable lacquer which is arranged on the parts which are not to be treated. The implant or its said parts are in electrical contact, via the holder, with the attachment 21' above the surface of the electrolyte. In the electrolyte, the said cathode 22 functions as a counter-electrode. This counter-electrode is made of suitable material, for example Pt, gold or graphite. The counter-electrode is preferably mounted on the holder in such a way that the whole arrangement is jointly fixed in the electrolyte bath 26. The anodic oxidation is obtained by applying an electrical voltage between implant/implant part/implant parts and counter-electrode, whereupon the implant or its part or parts in question are given positive potential. The implant, implant part/implant parts, the counter electrode and the electrolyte constitute an electrochemical cell in which the implant or its respective part forms an anode. The difference in electrical potential between implant/implant part and counter-electrode gives rise to a stream of negatively (positive) charged electrolyte ions to the implant or implant part (counter-electrode). If the electrolyte has been chosen suitably, the electrolyte reactions in the cell result in formation of an oxide layer on the implant or surface of the implant part. Since the electrode reactions also result in gas formation, the electrolyte should be stirred in a suitable manner, which is done with magnetic agitator 25, preventing gas bubbles from remaining on the electrode surfaces.

The formation of the titanium oxide layer and its final properties are affected by a number of parameters in the process, e.g. the electrolyte's composition and temperature, the voltage and current applied, the electrode geometry and the treatment time. The way in which the desired layers are produced is described in more detail below. Examples are also given of how the process parameters affect various properties of the oxide layers and how the oxide thickness and porosity can be varied.

To achieve the desired layer properties, one starts, for example, from a mechanically worked surface which can be turned or polished. Cast and pressed implants or implant parts can also be used. The surface is cleaned in a suitable manner, for example by ultrasound cleaning in organic solvents in order to remove impurities from previous production stages. The cleaned implant or the cleaned implant part is secured in the said container, which is secured together with the counter-electrode on the holder. The arrangement can then be immersed in the electrolyte. The two electrodes are thereafter coupled to a voltage source (not shown) and an electrical voltage is applied, whereupon the process commences. The process is terminated, after the desired time, by interrupting the voltage application.

Figure 6:
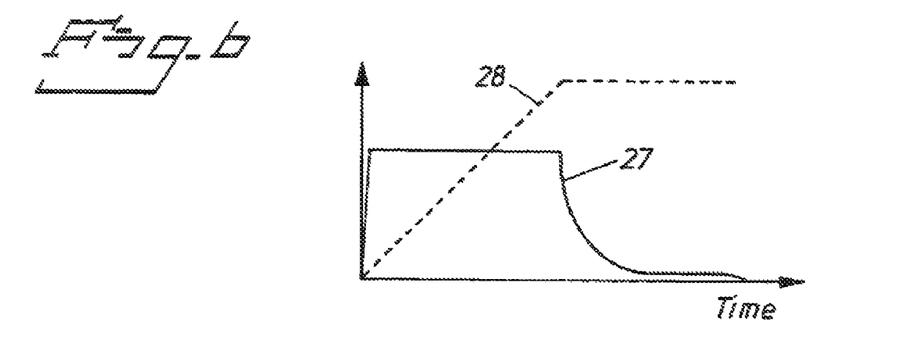
FIG. 6 shows, in diagram form, the voltage and current functions used in association with the oxidation process.

The electrical voltage can be applied in different ways, cf. also FIG. 6. In a galvanostatic process, the current is kept constant, the voltage being allowed to vary according to the resistance in the cell, whereas, in a potentiostatic process, the voltage instead is kept constant and the current is allowed to vary. The desired layers are formed preferably by using a combination of galvanostatic and potentiostatic control. Galvanostatic control is used in a first stage, the voltage being allowed to increase to a preset value. When this voltage value has been reached, the process changes over to potentiostatic control. On account of the resistance of the oxide layer which has been formed, the current drops in this state.

FIG. 6 shows the development of the current 27 and voltage 28 over time. The exact appearance of the curves depends on various process parameters and also reflects the formation of the oxide layer and its properties.

Up to a certain voltage, which is dependent on electrolyte, relatively thin oxide layers (<0.2 μm) are obtained, where the oxide layer thickness is approximately linearly dependent on the applied voltage, and independent of treatment time after the maximum voltage has been reached. These layers are essentially closed, and only in exceptional circumstances do they have a partially open porosity. For most electrolytes, the critical voltage is about 100 volts.

To achieve the desired porous oxide layers, it is necessary to apply considerably higher voltages in excess of 150 volts, typically 200-400 volts, depending on electrolyte. At these voltages, the oxide thickness is no longer linearly dependent on the voltage, and, instead, considerably thicker layers can be produced. For certain electrolytes, the oxide thickness at these voltages is also dependent on the treatment time after the maximum voltage has been reached. Suitable electrolytes for achieving porous layers using this method are diluted inorganic acids (e.g. sulphuric acid, phosphoric acid, chromic acid) and/or diluted organic acids (e.g. acetic acid, citric acid), or mixtures of these.

The implant which is treated in sulphuric acid has a surface with high density and open pores. Some 20% of the surface consists of pores or channels/channel branches, with sizes (diameters) preferably in the range of 0.1-0.5 μm. The thickness of the layer can be 2 μm. The implant which is treated in phosphoric acid has a similar density of pores. The pore size distribution can differ considerably. In the case shown, pore sizes can be chosen preferably in the range of 0.3-0.5 μm, but a good number of larger pores (up to 1.5 μm) can also be present on the surface. The oxide thickness in this embodiment is 5 μm.

Figure 7:
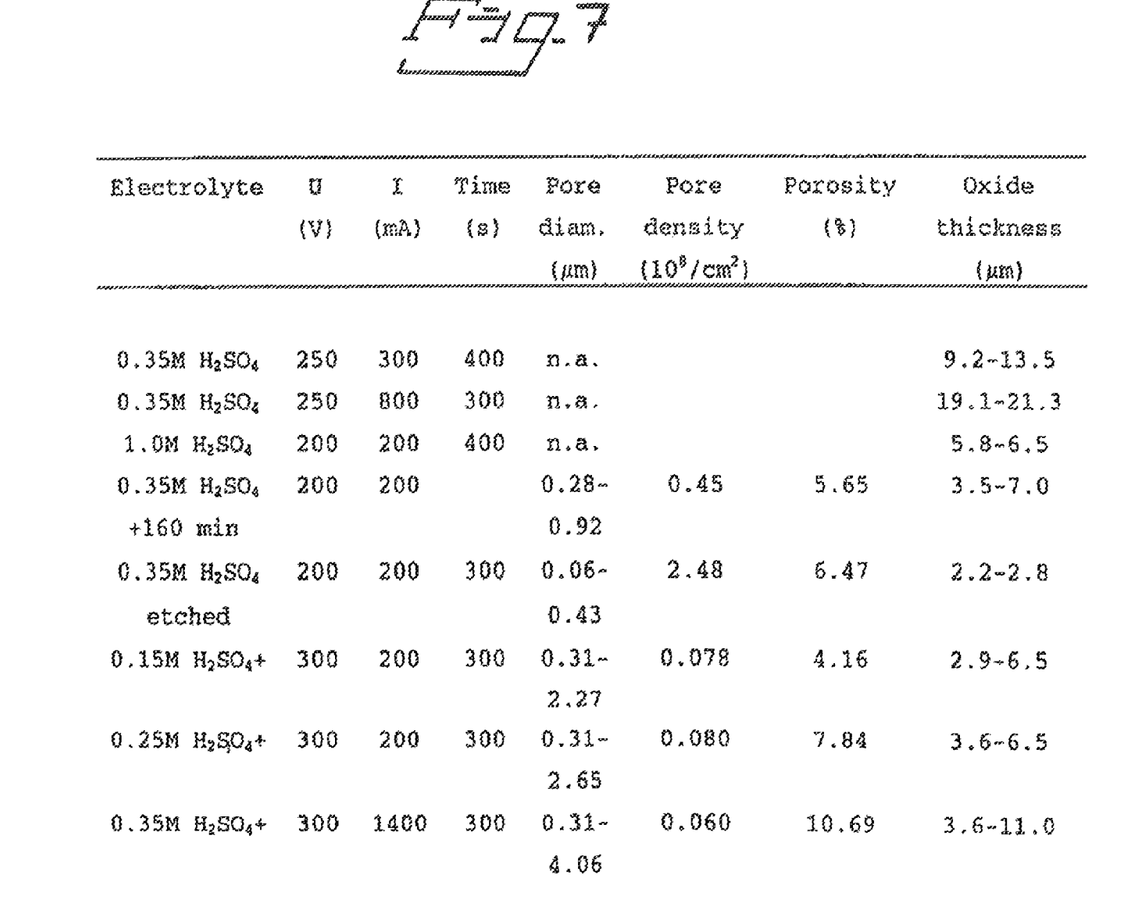
FIG. 7 shows, in table form, parameters for building up different titanium oxide layers.

The table according to FIG. 7 shows the structure of the oxide layer made with different process parameters in this method. The parameters shown are the electrolyte composition, voltage (volts), current (mA), time, pore diameter, pore density, porosity and oxide thickness.

The invention is not limited to the embodiment described above by way of example, but can be modified within the scope of the attached patent claims and the inventive concept.

We claim:

1. An implant layer for arranging on an implant for bone or tissue structure and which constitutes a boundary or barrier between the body of the implant and the structure for the purpose of increasing retention and which has, in this context, a thickness, wherein the layer is designed with a channel network which gives the layer a porosity, and wherein the channel network is designed with mouths which face towards the structure and whose respective cross-sectional diameters, at a surface of the layer which faces towards the structure, are less than the respective extents of the channels in and down into the layer as seen from the said surface and wherein the layer consists of or comprises a titanium oxide layer, wherein the mouths are bounded externally by lips, wherein the layer has a surface roughness, at its outer surface, in the range of 0.4-5 μm and wherein each surface has pores or channel mouth areas with diameters or surface area sizes in the range of 0.1-10 μm.

2. An implant layer according to claim 1, wherein the channel network comprises contiguous channel branches which extend through at least the greater part of the layer from the said surface and to a transition from the layer to the body of the implant.

3. An implant layer according to claim 1, wherein the channel network has channel branches which extend in directions which are different than the depth direction of the layer or the radial direction of the implant.

4. An implant layer according to claim 1, wherein the implant layer is established on an undulating or uneven surface present on the implant from the start and having a high roughness value, for the purpose of increasing the layer volume.

5. An implant layer according to claim 4, wherein the roughness value is from 0.4-5 μm.

6. An implant layer according to claim 1, wherein the implant layer has a thickness which gives a substantial corrosion resistance for the implant as a whole.

7. An implant layer according to claim 1, wherein the channel network is arranged with a mouth arrangement towards the bone or tissue structure, permitting increased bone growth penetration into the channel at the said mouths.

8. An implant layer according to claim 1, wherein the layer has an average thickness in the range of 0.5-20 μm.

9. An implant layer according to claim 8, wherein the layer has an average thickness in the range of 2-20 μm.

10. An implant layer according to claim 1, wherein the oxide layer has a high degree of porosity, with a number of $1 \times 10^7$-$1 \times 10^{10}$ pores/cm$^3$.

11. An implant layer according to claim 1, wherein the total channel network or pore volume lies in a range of $5 \times 10^{-2}$ and $10^{-5}$ cm$^3$.

12. An implant layer according to claim 1, wherein the implant consists of a screw implant for application in the jaw bone.

13. An implant layer according to claim 1, wherein the layer forms a depot for applied bone-growth-initiating or bone-growth-stimulating agent or substance.

14. An implant layer according to claim 13, wherein the agent or the substance migrates from the depot to the bone or tissue structure by means of concentration diffusion.

15. A method for producing, by anodic oxidation, on an implant comprising or consisting of titanium, thick oxide layers according to claim 1 on one or more titanium surfaces which are intended to be placed against or arranged next to one or more tissue and/or bone growth areas, where at least part or parts supporting the one or more titanium surfaces are prepared and immersed in electrolyte and the implant is brought into contact with an electrical energy source above the electrolyte surface and the oxidation process is established by also connecting to the energy source a counter-electrode arranged in the electrolyte, wherein diluted inorganic acids, diluted organic acids and/or small quantities of hydrofluoric acids or hydrogen peroxide are added to a composition of the electrolytic, and wherein the energy source is chosen to operate with voltage values of at least 150 volts.

16. The method according to claim 15, wherein the energy source is chosen to operate with the voltage valves in the range of 200-400 volts.

17. The method according to claim 15, wherein the voltage is varied at times for the same implant in order to create different channel or pore sizes within a same surface area.

18. The method according to claim 15, wherein a position of the implant in the electrolyte is changed together with the composition of the electrolyte and/or the voltage in order to create different oxide thicknesses and/or areas of different porosity or pore or channel characteristics.

* * * * *